United States Patent
Rost

(10) Patent No.: US 6,725,200 B1
(45) Date of Patent: Apr. 20, 2004

(54) PERSONAL DATA ARCHIVE SYSTEM

(76) Inventor: Irmgard Rost, Niebueller Strasse 19, D-90425 Nürnberg (DE)

( * ) Notice: Subject to any disclaimer, the term of this patent is extended or adjusted under 35 U.S.C. 154(b) by 596 days.

(21) Appl. No.: 08/793,984

(22) PCT Filed: Sep. 13, 1995

(86) PCT No.: PCT/EP95/03597

§ 371 (c)(1),
(2), (4) Date: Mar. 13, 1997

(87) PCT Pub. No.: WO96/08755

PCT Pub. Date: Mar. 21, 1996

(30) Foreign Application Priority Data

Sep. 13, 1994 (DE) .......................................... 44 32 533
Nov. 15, 1994 (EP) ........................................... 94118018

(51) Int. Cl.[7] ............................. G06F 17/60; G06F 5/00
(52) U.S. Cl. ................................. 705/3; 705/2; 705/17; 705/18; 235/380
(58) Field of Search ........................... 705/1–3, 41, 17, 705/18; 235/379–381

(56) References Cited

U.S. PATENT DOCUMENTS 4,709,136 A * 11/1987 Watanabe .................... 235/379

FOREIGN PATENT DOCUMENTS

| DE | 3815633 | 3/1989 | |
|---|---|---|---|
| DE | 4213797 | 10/1993 | |
| DE | G9018059.3 | 9/1994 | |
| FR | 2680258 | 2/1993 | |
| WO | 90/12464 | 10/1990 | |
| WO | WO 90/12464 | * 10/1990 | ............. H04L/9/00 |

OTHER PUBLICATIONS

"Transparent Connectivity with MHS–Based Applications", 1996 Copyright Lotus Development, an IBM subsidiary.*
Highland: "Microcomputer Security: Data Protection Techiques". In: 8246 Computers & Security, 4 (1985), Jun., No. 2, Elmont, New York, USA, pp. 123–134.
"PraxisComputer" [Office Computer], No. 4, Jun. 15, 1994, pp. 3–6.
"PraxisComputer" [Office Computer], No. 2, Mar. 10, 1995 pp. 8/9.

* cited by examiner

Primary Examiner—Jeffrey Pwu
(74) Attorney, Agent, or Firm—Venable LLP; Catherine M. Voorhees

(57) ABSTRACT

The invention concerns a personal data archive system with portable personal storage devices allowing the owner to enter and store personal data. Authorization checking devices are allocated to the storage devices and grant access to at least some of the personal data stored in the storage devices only in the event of a positive authorization and/or authentication.

41 Claims, 5 Drawing Sheets

PROCESSOR CHIP CARD

EMERGENCY CARD

PERSONAL INFORMATION:
LAST NAME, FIRST NAME, DATE OF BIRTH, ZIP CODE, CITY, STREET ADDRESS, TELEPHONE NUMBER (NO INFORMATION ON HEALTH INSURANCE, HEALTH INSURANCE NUMBER AND THE LIKE)

NOTIFY IN CASE OF EMERGENCY:
LAST NAME, FIRST NAME, ZIP CODE, CITY, STREET ADDRESS, TELEPHONE NUMBER (INFORMATION ON POSSIBLY ADDITIONAL AND ALTERNATIVE PERSONS)

ATTENDING PHYSICIANS:
LAST NAME, FIRST NAME, OFFICE ADDRESS: ZIP CODE, CITY, STREET ADDRESS, TELEPHONE NUMBER, PROFESSIONAL SPECIALIZATION (REFERENCE TO POSSIBLY ADDITIONAL PHYSICIANS)

MUST ABSOLUTELY BE NOTED:
DISEASES OR ANOMALIES IMPORTANT FOR EMERGENCY CARE, SUCH AS INTOLERANCE OF OR ALLERGY TO MEDICATIONS (NAME OF MEDICATION, INTERNATIONAL ABBREVIATION OF ACTIVE INGREDIENT, TYPE OF REACTION), DIFFICULTY WITH INTUBATION, INCIDENCES OF NARCOSIS, CEREBRAL SEIZURES, DIABETES MELLITUS, MARCUMAR THERAPY, RENAL INSUFFICIENCY, DIALYSIS TREATMENT, GLAUCOMA, CONTACT LENSES, ARTIFICIAL EYE, HEART PACEMAKER, VISCERAL INVERSION, CHOLINESTERASE DEFICIENCY, PORPHYRY, HEMOPHILIA, OTHER

BLOOD GROUP, Rh FACTOR:
BLOOD GROUP (A, B, O), RHESUS FACTOR: Rh-POSITIVE (D+)/Rh-NEGATIVE (D-),
ANTIBODIES

ORGAN DONOR CARD:
I AM AN ORGAN DONOR FOR TRANSPLANTS: YES/NO
IN THE EVENT OF MY DEATH PLEASE INFORM THE FOLLOWING: ADDRESS, TELEPHONE

LIVING WILL
IN THE EVENT OF A SERIOUS DISEASE OR SERIOUS ACCIDENT, AS AN EXPRESSION OF MY WISHES FOR MY FAMILY AND MY PHYSICIANS, I STATE THE FOLLOWING: ARTIFICIAL PROLONGATION OF LIFE: I HEREBY STATE THAT MY LIFE....
LOCATION, DATE, SIGNATURE
CARE INFORMATION:
THE FOLLOWING PERSONS ARE AUTHORIZED TO RECEIVE DETAILED INFORMATION ABOUT MY STATE OF HEALTH AND ABOUT DIAGNOSTIC AND THERAPEUTIC PROVISIONS FROM THE PHYSICIANS HANDLING MY CASE.
FOR THIS GROUP OF PERSONS, I EXPRESSLY RELEASE THESE PHYSICIANS FROM THEIR OBLIGATION TO SILENCE: NAME, ADDRESS, TELEPHONE NUMBER.
IN THE EVENT THAT I CANNOT RESPOND OR AM UNABLE TO MAKE A DECISION, I GIVE THE FOLLOWING PERSONS THE POWER TO NEGOTIATE FOR ME UNDER THE LAW REGARDING MEDICAL CARE AND IN ACCORDANCE WITH MY LIVING WILL, AND TO GIVE OR DENY APPROVAL FOR MEDICALLY NECESSARY PROVISIONS AND OPERATIONS:
NAME, ADDRESS, TELEPHONE NUMBER

LOCATION, DATE, SIGNATURE

FIG. 2B

PROCESSOR CHIP CARD

PATIENT CARD:

PATIENT HISTORY:
YEAR/DISEASE OR OPERATION
OPTIONAL: ICD KEY
STORAGE IN DIGITAL MEMORY (FOR INSTANCE ON MID-DATA)

DIAGNOSTICS:
LABORATORY TESTS (DATE, SUBSTANCE EXAMINED WITH UNIT OF MEASUREMENT, FINDINGS), SONOGRAMS, X-RAY, COMPUTER TOMOGRAPHY, MRI, FUNDUS PHOTOGRAPHY, EKG, EEG, SPIROMETRY, BODY PLESTHYSMOGRAPHY, OTHER: DATA ON THE EXAMINATION, BODY REGION EXAMINED, STORAGE ON DIGITAL MEMORY (FOR INSTANCE ON MID-DATA)

IDs:
IMMUNIZATION RECORD, ALLERGY CARD (ALLERGY TO INHALANTS, FOODS, CONTACT SUBSTANCES AND MEDICATIONS), DIABETIC ID CARD, BLOOD PRESSURE CARD, CARD REPORTING ON ANTICOAGULANT TREATMENT (MARCUMAR), PACEMAKER CARD, CARD REGARDING THE ADMINISTRATION OF BLOOD AND BLOOD PRODUCTS

LONG-TERM DIAGNOSIS:
DIAGNOSIS ONLY OF DISEASES WITH A CHRONIC OR LONG-TERM COURSE: DIAGNOSIS, ICD KEYS (FROM SOFTWARE DATA BANK)

LONG-TERM MEDICATIONS:
ONLY MEDICATION TO BE TAKEN OVER A LONG PERIOD OF TIME: TRADENAME, INTERNATIONAL ABBREVIATION FOR THE ACTIVE INGREDIENT, DOSE ORDERED (FROM PROGRAM DATA BANK)

CHECKUPS:
DOCUMENTATION OF CHECKUPS OF CHILDREN, PREGNANT WOMEN, EARLY DETECTION CANCER EXAMINATIONS, WELLNESS EXAMINATIONS (CHECKUPS)

FOLLOWUP OF TUMOR DISEASES:
DOCUMENTATION OF APPROPRIATE PHYSICIAN FOLLOWUP PROGRAMS FOR MALIGNANT TUMOR DISEASES, FOLLOWUP PROGRAMS (FROM SOFTWARE DATA BANK)
FOLLOWUP OF CHRONIC DISEASES:
DOCUMENTATION OF APPROPRIATE PHYSICIAN FOLLOWUP PROGRAMS FOR CHRONIC DISEASES, SUCH AS HIGH BLOOD PRESSURE OR DIABETES MYELITIS, FOLLOWUP PROGRAMS (FROM SOFTWARE DATA BANK)

GENERAL HEALTH PROGRAMS:
A SERIES OF PROGRAMS (FROM SOFTWARE DATA BANK) THAT ARE SUITABLE OVERALL TO PRESERVE HEALTH, SUCH AS DIET PROGRAMS FOR THE OBESE, NONSMOKER PROGRAMS, SPECIAL EXERCISE PROGRAMS, EDUCATIONAL PROGRAMS FOR DIABETICS, ETC.

FIG. 2C

PERSONAL DATA ARCHIVE SYSTEM

BACKGROUND OF THE INVENTION

The invention relates to a personal data archive system defined generically as having portable storage devices containing at least one first memory device and a separate second memory device and authorization checking devices associated with the portable storage devices through which access to at least some of the data stored in the portable storage devices can be enabled as a function of positive authorization and/or authentication.

In many areas of daily life, personal data is needed, which however are often not available in collected form, so that it must be looked for and assembled tediously each time it is needed. Often information is lost in the process or fails to be taken into account.

Merely as an example of this, patient data can be cited on the basis of which some problems of existing archiving systems will be discussed below as examples. The medical data of a patient is acquired and documented by many parts of the health care system. In the form of documentation practiced so far, using written entries in doctor's certificates, file cards, badges and ID cards (such as a diabetic ID card) and the exchange of information as practiced until now by transmittal of physician's and hospital discharge reports, important medical data is often lost.

For instance, if a patient changes doctors, the data acquired until then typically remains in the card file of the last doctor to treat him, and the next doctor begins to collect data all over again. A further factor in modern medicine is an increasing split in medical care among the various professional specialties; there is often inadequate communication, if any, among professional colleagues involved in an individual case.

In the information system employed thus far, diagnostic tests are therefore often repeated, because the physician treating the patient later has only written assessments of his predecessor about previous examinations, but does not, for instance, have the original X-rays or ultrasound images or laboratory reports or other test records. Because of the possibilities for different interpretations in an individual case, a physician would understandably prefer not to dispense with his own assessment of original documents in deciding what measures to take later.

Another serious disadvantage of the existing information exchange with regard to patient data resides in the fact that important medical data is often unavailable in an emergency. It is true that in the past a number of ID cards and badges have been developed, examples being the European emergency ID card, immunization record, Marcumar card, allergy card, and so forth; but disadvantageously, if the patient is even issued such documents, important data is still spread among various papers, and their contents, if it is lost, usually can not be reconstructed.

Progress in information technology in the field of health care could be provided by patient cards in the form of magnetic strip or processor chip cards that are capable of storing medical information on a portable electronic data carrier. Thus several card projects have arisen recently that have as a goal the use of processor chip cards to store data in the medical field.

However, the developments of patient cards known thus far have not led to any substantial improvement in data bases for immediate patient case, since because of the limited storage capacity of the processor chip card, only a small proportion of a patient's medical data can be taken into account. The "Diabcard", for instance (GSF Forschungszentrum fur Umwelt und Gesundheit Medis-Institut, P. 0. Box 1129, D-85758 Oberschleißheim, Germany) contains only the medical data relevant for care of the diabetic. In another model project, which was started by the Kassenärztliche Vereinigung Koblenz, [,HMO, Koblenz], the Zentralinstitut fur die kassenärztliche Versorgung [Central Institute for HMO Care] and the Bundesvereinigung Deutscher Apothekerverbände [Federal Association of German Pharmacists' Organizations] in the cities of Neuwied and Andernach ("PraxisComputer" [Office Computer], No. 4, Jun 15, 1994, pp. 3–6 and No. 2, Mar. 10, 1995, pp. 8/9), all that the data set stored on a patient card includes, besides the patient history data, is the immunization record and X-ray status, and medications issued to the patient by the pharmacist.

Another significant disadvantage of existing memory cards is that the stored data are not effectively protected against misuse. Purely encrypting the stored information is inadequate;, since if enough effort is exerted, any code can in the final analysis be deciphered. In the case of patient data, this means that patient data kept by the patient himself can easily fall into the hands of unauthorized persons who can use the information, after decoding the data, to the detriment of the patient.

From German Utility Model DE 90 18 059 U1, a system is known for storing, furnishing and updating fixed and/or variable patient and treatment data. Its point of departure is a stationary central computer unit with a storage unit in which the patient data, present in a patient card file, is stored in the form of patient-specific data sets, and a data interface for input/output of patient data combined with a portable unit, such as a portable computer, that is intended to hold selected patient data sets, or all the stored patient data sets. Thus a physician, even in house calls, can use the information in his electronic patient card file and keep it updated directly, even away from his office. An individual patient data set can be called up via a health insurance card and activated, so that the administrative data on the patient visit can be acquired directly. Once the physician is back in his office, he can then update the data on his stationary central computer unit by means of the portable unit.

Thus the physician takes his own data set along to the patient, instead of having to get the patient's collected data from various physicians and clinical entities from the patient himself. Emergency medical services, for instance, are therefore unable to use this system for patients unknown to them. In other words, users, rather than the persons to whom the data pertain, store only limited data portably, and only temporarily.

German Patent DE 38 15 633 C2 discloses a data processing system for central processing of medical data. In it, portable personal storage devices are used, which are designed f,or temporary storage of continuously acquired biodata. At least at predetermined time intervals, the stored data is therefore transmitted by telephone to the data processing system of a hospital. In these storage devices, security aspects therefore play no role.

These above two references accordingly provide no solutions with respect to noncentralized archiving of personal data that go beyond typical portable storage devices.

In other areas of life as well, the assembly, manipulation and availability of personal data is a tedious process and often does not lead to the fully comprehensive results sought. Besides the often inadequate storage capacity of the data memories available on processor chip cards for the desired quantity of data, there is a risk, in storage on portable mass stores, of misuse because of the lack of access security.

SUMMARY OF THE INVENTION

It is thus the object of the present invention to create a personal data archive system that includes portable personal storage devices in which the owner can store and preserve personal data and that enables a higher security standard than systems known from the prior art.

This object is attained with a personal data archive system of the generic type described above where the portable storage devices contain personal data of a single owner and the personal data stored in the second memory device is accessible only in combination with the first memory device assigned to the owner of the portable storage devices and only as a function of positive authorization and/or authentication by means of the authorization checking devices.

Thus in a generic personal data archive system, the invention provides that the storage devices contain personal data of a single owner and that associated with the storage devices are authorization checking devices, by means of which access to at least some of the personal data stored in the personal storage devices can be enabled only as a function of a positive authorization and/or authentication.

In particular, the invention overcomes the security disadvantages of the prior art. Data misuse is thus largely impossible or at least unprofitable in view of the effort required.

Because according to the invention access to at least some of the data is possible only after authentication and authorization is obtained, it is assured that the data, possibly encrypted as well, are inaccessible to unauthorized persons seeking to decode these data to obtain information.

If this kind of authorization-dependent access is not contemplated for all the data regions, then it is also possible to store data that is freely accessible, which can be advantageous in the case of emergency data, for instance.

Another substantial advantage is that the invention also creates the possibility of storing relatively large amounts of personal data noncentrally with adequate security; to that end, portable storage devices with relatively large storage capacities can be integrated into the system. In the past, as long as the desired security of the stored data against unauthorized access could not be achieved, there was no sense in storing such significant personal data within accessible range of each person himself, for data protection reasons. It is the present invention that first makes it possible for even large quantities of data to be adequately protected, so that for the very first time, it is appropriate to tie together correspondingly sufficiently large storage media, as has been done for instance by means of preferred embodiments of the storage devices of the invention. In other words, from the technical standpoint of storage, while fundamentally there is no difficulty in furnishing mass stores for large quantities of data, nevertheless such storage media do not offer the requisite access security for personal data that has now been created by the invention.

For instance, access to the stored data and the scope of this access can be determined, for instance accepting stored emergency data, solely by the owner of the storage devices.

The security devices in the personal data archive system of the invention, that is, the authorization checking devices, can begin with a mutual identification of storage devices and access peripherals and can proceed, by way of the registration of a user ID code by the authorization checking devices, to message encryption and authentication, for instance by means of an electronic signature.

As a result of the security options included in the scope of the invention, an extremely high level of data security is attained, of the kind that until now, not only in the medical field, had been unattainable.

The invention also has the advantage that automatic data processing hardware, for instance, that is already available at a favorable price as a mass-produced product can be used; this allows suitable estimation of the financial outlay and keeps it within sensible low limits. By means of suitable interfaces with currently used medical practice office administration programs, the aforementioned typical hardware or special hardware and suitable software can easily be incorporated into the existing office data processing system of a physician or clinical entity; in the Federal Republic of Germany, for instance, this is assured via the existing interface known as "Behandlungsdatenträger (BDT) [Treatment Data Carrier]".

For instance if the invention is used as a patient data archive system, then direct personalizing and updating of relevant data can be done in the doctor's office itself. Even now it can be predicted that medical data in the future will be acquired and stored increasingly primarily on digital media, for instance. In the system of the invention, the patient is made capable of having the data copied directly to his own storage medium even in the doctor's office, and thus applies particularly to medical data for ID card functions and the listing of diagnoses and long-term medications. Other more-extensive text and image data, as an alternative to being copied onto the patient-specific storage devices in the doctor's office, can be digitized in personalization offices and written onto the storage devices. Optionally, prior to digitization, a reduction in size or even microfilming can be performed, to reduce the storage space required.

An alternative to the portable personal storage devices in multimedia data communications may be a generalized data association in outpatient medicine, which could be achieved for instance using the ISDN network. To some extent, this is already being tested in hospitals, research institutes and universities. These projects primarily involve teleconsultation, that is, the exchange of diagnostic image material, for instance, for the sake of consultative findings. In this field, there are still other useful perspectives, such as telecommunications in the administrative field or teletherapy.

In outpatient medicine, however, there are completely different prerequisites and goals. In outpatient medicine, the patient comes to the doctor, or vice versa. The patient can easily function as a supplier of data, and thus entails no cost whatever of the kind that would be involved in comparison with data networking. In data exchange networking, there is also the risk that products and services will be directed to what is technically feasible, so that the actual requirements of the patient are forgotten.

In telemedicine, considerable problems in acceptance must be expected. Exchanging personal medical data via data highways creates in the patient the—perhaps not unjustifiable—fear of being the "transparent patient". Moreover, in remote data transmission, unauthorized persons could be capable of accessing, the stored data.

Another useful possibility offered by the present invention, however, is of synergistically combining the personal or in particular patient data archive system with telemedicine. The personal storage devices, such as a processor chip card in combination with a portable mass store, with the inclusion of suitable access peripherals, can all act together as a peripheral station and, once writing access has been enabled, can receive patient-related data from various sources. Or in the opposite direction, a physician asked for a consultatation can access the data of the storage devices over the ISDN network, for instance, as soon as the authorization identification has been made. In still another application, a patient, through a personal access peripheral, in a telephone call to a physician can make his data available from the storage devices for instance parallel to the conversation, over the second channel of the ISDN connection, thus providing the access enablement by way of his own authorization.

Another advantage of the present invention is that existing data systems and structures can easily be adopted and expanded. For instance, in a patient data archive system, by the adoption of existing protocols for data exchange between the health insurance card, already introduced in the Federal Republic of Germany, and the associated reader, a freely accessible region of the storage devices—preferably a processor chip card functioning as a kind of text or text recording card—can be read in the reception area of any doctor's office or in the admitting office of any hospital in Germany. The access to the emergency data is not protected, at least against access by physicians, so that these data are accessible even if the patient is unconscious. Alternatively, an access peripheral identification can be built in to provide a certain amount of protection of emergency data; in that case, physicians and rescue services will have suitable access peripherals available. The authenticity checking or authenticity tracking then refers to the reader itself, for instance. The processor card, which is an example of a suitable storage device component, in that case ascertains independently of the user whether the particular reader has authorization for access. This check embodied in this way can also be used for other data regions besides the emergency data region.

Another possibility of protecting the data that pertain to care in a medical emergency in a way that does not hinder an emergency situation, so that the data are accessible without major effort to only a limited group of persons, is provided by a physician's card through which a corresponding access enablement is achieved. With the physician's card, generally known as a "professional card" or authorization card, a per son who per se is authorized access can in a sense log into a reader. Until the person logs out, the data thus released can be read from the storage devices by the reader. Thus the access authorization of persons providing medical services can be regulated in a person-specific way.

In any case (including the case described above), it will be noted after an access, on the processor card provided for instance as a component of the storage devices, a notation will be made as to which reader or professional card was used for access to the processor card. Thus it is possible to ascertain which reader was used to gain access, for instance the reader in a particular ambulance. The name of the responsible physician can then be ascertained from the duty schedule. If an authenticity check has a positive outcome, then the authorization for memory access is also effected simultaneously, for instance by the processor card itself.

Only the other data, for instance on the text card and on an image or image recording card, as a mass store that is formed by a mass store can for instance be called up only after a personal identification number (PIN) known only to the patient is entered. The patient enters the PIN via a separate number keypad in the doctor's office. On the processor card, for instance, as an authorization checking device component on the one hand and as a storage device component on the other, a kind of table of contents of all the storage devices is stored.

Current examination findings, such as laboratory reports or blood pressure figures, data for checkups and followup examinations, ID cards, etc., can be added to it at any time by the treating physician directly in the office visit for the sake of ongoing documentation. Health insurance entities, for instance, can also send updates, which can be installed by means of separate equipment, either in the physician's office or at the health insurance office. This data can be in encrypted form, for instance, on a mass storage medium. Only by means of a chip card-supported or -enabled access can these data be deciphered, in an exemplary embodiment; to that end, on account of what may be a very large amount of data, a coprocessor, which for instance is also disposed on the chip card, is used as a crypto unit.

In an advantageous further feature of the invention, a plurality of checking stages can be performed by means of the authorization checking devices. The advantage attainable as a result is that the stored data can be protected in graduated fashion against unauthorized accesses. For instance, it may be desirable that a pharmacist, can access information on medications administered previously, at least in the presence of the owner himself, or a bank employee in a bank transaction can transfer long-term credit and debit authorization data to the data bank of the new institute, or a taxi driver can have the exactly designated destination address shown on his display, so that he will not drive to the wrong destination because of an error in understanding, or fail to recognize the destination, etc.

In a preferred embodiment of the invention, at least one group of storage devices is formed by a storage medium that can be written and in particular rewritten by adding and/or modifying personal data. Thus advantageously the stored information can be kept updated without problems, without continually having to produce new complete storage devices again each time modifications or additions of data are made, which does have advantages with a view to maximum possible security, depending on specific applications. A rewritable storage medium has the advantage that the existing memory space can be optimally utilized, since unnecessary or obsolete data need not be kept stored. A storage medium that is writable only once has the advantage that data cannot be deleted by mistake and thus irretrievably lost.

Because the authorization checking devices are designed to enable reading and/or writing access to the writable storage medium as a function of an appropriate authorization and/or authentication, which may include an associated checking step, it can advantageously be assured that the access authorization can be handled in a manner that suits the medical office best. This is equally true for the case in which at least some of the writable storage medium is write-protected or write-protectable, as is provided in a further feature of the invention.

If the storage devices include a first group and at least one second group, in particular with different storage capacities, then a rough classification of the data to be stored or of the stored data can be made; for instance, a small, high-speed memory can advantageously be used for frequently used data, and a large, slow memory can be used for large amounts of seldom-needed data. Moreover, one memory can contain information required for decision-making on the part of the authorization checking devices, thereby also protecting the other memory.

In a preferred embodiment of the invention, the first group of storage devices is in particular the smallest group in terms of capacity and is an ID, identification or master data storage group. In a practical way, in accordance with a further feature of this version, the personal data, such as ID, identification or master data, stored in the first group of personal storage devices are accessible independently of the authorization checking devices or upon positive authorization and/or authentication in a first checking step of the authorization checking devices. Thus a memory is available that is suited to storing emergency data, which ought to be accessible even without the collaboration of the owner.

An especially preferred embodiment of the invention is such that only in combination with at least the first group of storage devices can the at least one second group of storage devices be accessed.

In a further feature for instance of the above embodiment, it is preferred according to the invention that the second group of storage devices, of greater capacity than the first group, is a detail data storage group, whose contents are thus especially secure. This security can be increased still further by providing that personal data, such as detail data, stored in the second group of personal storage devices, are accessible only as a function of a positive authorization and/or authentication, optionally in a second checking step, by means of the authorization checking devices.

Another especially preferred realization of the invention is that the at least first and second groups of storage devices are formed by separate first and second memory devices, in particular in different first and second data carriers. The spatial separation of the storage device groups, in, particular on separate data carriers, advantageously and in an especially simple way contributes to high security of the system of the invention, since this makes it possible to store the data carrier having the critical data securely as long as it is not needed, as it relatively seldom is. The system can also be set up in such a way that, as noted earlier above, access can be gained to the second group of storage devices only in combination with the first group of storage devices. If care is taken so that both groups of storage devices are not lost at once, then the data on the second group of storage devices is absolutely secure.

In preferred features of the invention, the first group of storage devices or the first memory device is a magnetic, magnetooptical or optical memory area or memory chip, especially on or in a preferably approximately credit-card-sized plastic card as the data carrier. Moreover, the second group of storage devices or the second memory device is an electronic, magnetic, magnetooptical or optical mass store (such as an optionally writable CD ROM, or WORM, for "Write Once Read Many"), in particular in the form of a 2.5 inch or 3.5 inch diskette or a semiconductor memory of a PCMCIA unit (PCMCIA=Personal Computer Memory Card International Association), as the data carrier. As such a combination, a processor chip card can for instance be used with the authorization checking devices, and a smaller memory and an MO (magnetooptical) disk can be used to store large amounts of data, including images; access protection for the MO disk is accomplished by the processor chip card, since at least the processor chip card must be present in order to gain access to the MO disk.

The distribution of medical information, for instance, among a processor chip card and a mass storage medium assures an intrinsically graduated data access and hence high security, which is still further increased by providing that the chip card in a certain sense functions as a key, for access on the one hand to the data stored on this chip card itself, an d on the other to the data stored in the mass storage medium.

In addition, the data in the mass storage medium may be encrypted, to assure even higher security.

Information that is in written form is stored on the text card, which by its own "intelligence" provides the access protection for both data carriers, for instance including encryption algorithms, while the image card takes over the task of storing large amounts of data, i.e. of images (X-rays, sonograms and endoscopy images, etc.), biosignals (such as EKGs, EEGs), or texts comprising patient history for which there is no more space on the processor card. In particular, in a patient data archive system, the text card can contain such information as administrative data, an emergency ID card, patient history, findings, checkups and followups, and a pass and the like.

For the invention, however, it does not matter whether or perhaps how the storage media are put together, but merely that effective data protection is accomplished. For instance, a very large-capacity optical memory can also be used as the sole memory and can be accommodated on a plastic card about the size of a credit card. By physically burning holes, storage capacities in the range of 1 gigabyte per $cm^2$ of sheet plastic as a data carrier are possible, so that for a card designed in this way, external mass stores are unnecessary.

One preferred design according to the invention provides that processor devices are associated with at least one group of storage devices and are preferably disposed on the data carrier, such as a plastic card, and in particular contain a processor. Especially advantageously, such processor, devices can be used for the authorization checking devices. The processor devices thus by their own "intelligence" assure access protection for the storage devices. It is also preferred that the processor devices are designed for controlling at least some groups of the storage devices and/or for at least partial control of accesses thereto, and/or in particular are designed as a group of authorization checking devices.

To increase data security, it is also advantageous if the storage devices are preceded by crypto devices, whose operation can be enabled in particular by means of the authorization checking devices for processing accesses to the storage devices. In other words, encryption and decryption of the storage data depend on enablement of access by the authorization checking devices. Preferably, the crypto devices are contained in the processor devices that may be present, and they preferably have a crypto processor.

If some of the storage devices and/or the authorization checking devices are realized on a processor chip card, then for instance the latter may also include a crypto unit. However, it is also possible for processor devices to be accommodated entirely or partly in an access peripheral or in associated computer devices.

In general, crypto devices may for instance employ an asymmetrical encryption method (RSA).

To prevent unwanted copies of the stored data from being made, a continuation of the invention contemplates that copy protection devices are provided, by means of which storage of, at least some data that are stored in the personal storage devices, and in particular in the second group thereof, on memories external to it can be prevented, and/or a storage of at least some data that are stored in the first group of storage devices, in memories external to it can be allowed. This last makes it possible for instance to copy the patient's name, address, and health insurance data without difficulty for use in writing prescriptions and billing for treatment.

Printout detection devices that may be provided work in a similar way; by means of them, a printout of at least some data that are stored in the personal storage devices, and in particular optionally the second group thereof, can be prevented and/or printing of at least some data that are stored in the first group of storage devices can be allowed. This last makes is easy for instance to produce a written treatment report for a physician.

To prevent the access, granted to one person, to the data by hardware devices from being unintentionally accessible to other persons, for instance via additional screens or by means of network cards or even other computers, output limitation devices should be provided, by means of which an output of at least some data that are stored in the personal storage devices, especially possibly in the second group thereof, in more than one output medium can be prevented.

On the other hand, to allow copying, printouts, multi-screen displays, network transmission, etc., of the data called up, the appropriate aforementioned protection devices can be neutralized by means of the authorization checking devices by means of a suitable positive authorization and/or authentication, optionally in an associated checking step.

A simple, fast and effective security device comprises the fact that the authorization checking devices are designed to incorporate peripheral identification (ID) codes of access peripherals for manipulating the storage devices into a checking operation for the sake of authorization and/or authentication, optionally for performing in particular a first checking step. This kind of authorization checking may be adequate for enabling access to emergency data, for example, and can be realized reliably by furnishing appropriate access peripherals to emergency medical technicians or their vehicles.

In addition or alternatively, the personal storage devices may have ID codes that can be incorporated by the authorization checking devices into a checking operation for the sake of authorization and/or authentication, optionally for performing in particular a first checking step. Thus one can be assured that these are not counterfeit storage devices, for instance, whose false data could dangerously, in the medical field, lead to the wrong treatment. Once again, this clearly shows how important it is, for instance in the field of patient data archiving, that the correct data be reliably furnished.

The security components preferably used in the present invention are user and/or owner identification, or an ID code of at least one user or the owner whose data are archived in the storage devices. Such ID codes are incorporated by the authorization checking devices into a checking operation for the sake of authorization and/or authentication, optionally for performing in particular a second checking step and optionally further checking steps to enable an access to at least some of the personal data stored in the personal storage devices.

Especially simple possibilities for inputting user ID codes, such as a user or owner identification, for the authorization checking devices effected via manual and/or electronic inputs, for instance from an authorization card.

To make it possible to associate information accesses and entries done at any time with a particular person, it is advantageous if accesses, allowed by the authorization checking devices, to the storage devices having the data relevant thereto such as peripheral ID codes of access peripherals and/or user and/or owner identifications, are documentable, in particular in the storage devices themselves.

To make the information contained in or on the storage devices accessible to the owner of these storage devices, or to allow him to update at least certain data himself, personal access peripherals are provided in a preferred embodiment of the system of the invention; by means of these peripherals, the owner whose data is archived in the storage devices, and/or users of the storage devices, as a function of an in particular appropriate authorization and/or authentication, optionally in an associated checking step, can access at least some of the archived data for the sake of information, data modification/supplementation, and/or transmittal, including via remote data transmission. Thus even in telephone consultations, agreements, orders, etc., it is easily possible to make the required data available to the other party to the conversation. Such remote data transmission is promoted by the two-channel ISDN network, for instance, in which speech and data transmission are already simultaneously possible.

For customer, patient and client visits on the one hand, and for work in a company, medical or legal practice of business office on the other, it is also advantageous if mobile and/or stationary access peripherals are provided, by means of which, as a function of an in particular appropriate authorization and/or authentication, optionally in an associated checking step, users can access at least some of the archived data for the sake of information and/or data modification/supplementation. As a result, the system can be kept ready for use anywhere and anytime, and rescue vehicles, police cars, etc. can for example easily be equipped so that they can utilize the stored information wherever they are.

With respect to the costs of the access peripherals, it is advantageous that these peripherals are for instance basically designed for writing and/or reading access, and access can be gained to at least some of the personal data stored in the personal storage devices as a function of an in particular appropriate authorization and/or authentication, optionally in an associated checking step.

For the especially simple authorization checking mentioned above, it is contemplated that the access peripherals have peripheral ID codes that can be detected by the authorization checking devices for checking a authorization and/or authentication, optionally for performing in particular a first checking step, and that the peripheral ID code is preferably activatable by means of a user ID code that can be input into at least one access peripheral.

The system can be structured especially economically and simply if conventional computer devices, such as PCs, are provided for driving the access peripherals. A favorable structure of the personal data archive system according to the invention is promoted by providing that depending on the formats of data carriers receiving the storage devices, the access peripherals contain card readers for instance for magnetic strip cards or chip cards, disk drives for magnetic, magnetooptical or optical diskettes, for instance, CD ROM drives, and/or receptacles for PCMCIA units, as are already especially widely available. This does not create a security risk, since the security of the data is assured by the authorization checking devices. Moreover, conventional computer devices including at least a screen, keyboard and printer, can be provided economically as the data display and input/output equipment.

An especially efficient, secure and reliable embodiment of the access peripherals and a corresponding operation of the system of the invention contemplates that at least two access peripherals are combined, in particular into one overall apparatus, to interconnect corresponding data carriers of the storage devices, and this combination is detectable, by the authorization checking devices to prove authorization or optionally as a first checking step. For example, a combined access peripheral for a processor chip card and a mass store can be provided as components of the storage devices. The authorization checking devices here may be realized especially simply, since the circuit can be predetermined in a fixed way. In particular, the storage devices in the form of the authorization checking devices can be operated independently of the operating system of a computer used for control, operation and evaluation purposes. Above all in this embodiment, but in principle in all the other suitable features of the invention, an access peripheral ID code can be used especially simply and efficiently for data protection.

First, an authorization of the user can be done. Access to the storage medium is allowed only if the access peripheral, used, which may be a suitable disk drive, in particular for two data carriers, such as a processor chip card and a minidisk, is equipped with an ID code. This assures that only properly equipped access peripherals, which may even be designed for only a single data carrier, can be used for writing and/or reading operations, which assures that access to the data of the storage devices will be obtained only by devices authorized for that purpose.

In an exemplary embodiment of the invention, both the reader of a processor chip card and the disk drive of a diskette each have an ID code, for the sake of data protection. The diskette is readable only if the reader ID codes authorizes the processor chip card, and if at the same time the disk drive ID code authorizes the diskette and at the same time the processor chip card enables the diskette.

Via the access peripheral ID code, it is also possible for every access to the data of the storage devices to be documented. This would be done in such a way that when using the access peripheral, such as a single disk drive or a combined disk drive for a plurality of memory devices, the appropriate ID code is left behind in the form of a stamp on a storage space intended for that purpose, such as on the processor chip card as part of the storage devices.

Finally, by way of the recorded access peripheral ID code, it is possible to identify the user. It is thus possible to, track where, that is, in which doctor's office or rescue vehicle, access to the data of the storage devices was gained. By suitable provisions, such as changing the ID code by turns, the authentication of the user can also be provided for.

To prevent a data carrier crash—which while not worrisome from the standpoint of security is certainly extremely unpleasant from the standpoint of information—from impacting negatively on data archiving, backup copies of all data carriers should be made and preserved. Preferably, the access peripherals are designed to produce backup copies of the portable personal storage devices, without evidence of authorization or optionally in a first checking step. Special safety provisions therefore need not be taken, since the same rules as for the originals govern access to copies of the storage devices.

For a preferred use of the personal data archive system of the invention, certain adaptations in manipulating patient data are advantageous, such as that the system is designed for entering and storing patient data, including written and graphic documents, with the owner. To that end, the system may include suitable input media, such as a scanner.

Preferably, the first group of storage devices includes an emergency data storage region, in which administration data and the data of an emergency card, organ donor card, emergency living will, and the like of the owner can be stored. Access to these data should be enabled by the authorization checking devices, freely or only with a physician or rescue service ID code, which can preferably be input via a special physician or rescue service card or a physician/rescue service access peripheral ID code into the authorization checking devices, or only with an owner ID code.

It is also preferred that the first group of storage devices includes an overview data store region, in which a listing of important patient history data can be stored, including any administration of blood or blood products that may have been made and a documentation of important health and disease data, including allergy, immunization, X-ray, pacemaker, diabetic, and medication data and the like, analogously to a patient's medical card. In addition to the access authorizations described above in conjunction with the emergency data, an access by health insurance organizations by means of a suitable ID code may also be provided for.

All these accesses can moreover be set up for a treatment data storage region included in the first group of storage devices, in which region a predetermined time frame and a predetermined content structure of checkups as well as examinations in the context of followup of chronic and/or malignant diseases can be stored, and for an optional or additional tracking data storage region, which is contained in the first group of storage devices and in which at least a predeterminable number and/or type of accesses to the storage devices, in particular including the preferably individual authorization and/or authentication that may have been performed and the type of access performed, can be stored individually.

A preferable embodiment of the first group of storage devices may include a documentation region, in which the relevant health and sickness data occurring over the course of the life of the owner of the storage devices can be stored, including patient history, diagnoses, findings such as laboratory reports, blood pressure figures, and so forth.

A preferable embodiment of the second group of storage devices may include a documentation region, in which all the original documents of medical records, reports, X-ray, ultrasound, computer tomography images, endoscopy images and so forth, biosignals, such as EKG and EEG data, etc., can be stored directly or in the form of graphics and the like.

An access to the aforementioned documentation regions can be enabled at least to such an extent by the authorization checking devices, individually or in combination with a physician ID code, which can preferably be input via a special physician card or a physician access peripheral ID code into the authorization checking devices, or with an owner ID code and/or a health insurance ID code.

In a preferred feature, the second group of storage devices, too, can contain a tracking data storage region, which in principle functions identically to the tracking data storage region in the first group of storage devices. An advantageous further development of this feature provides that the tracking data storage region is embodied in the manner of a shift register in the first group of storage devices, so that the oldest content therein can be shifted, in particular for final storage in the tracking data storage region of the second group of storage devices, to create space for a new entry in the tracking data storage region in the first group of storage devices. Thus the tracking data can be stored at any time. In particular, in applications of the personal archive system in other fields, it may be provided that only the last three to five items of access information continue to be stored, while older access information is erased.

Advantageously, an existing card widely used by the public, such as a health insurance card, personal ID card or ATM card, can hold all or some of the storage devices of the personal data archive system according to the invention.

To further increase security of the archived data, it is preferred that by means of the authorization checking devices, an ID code change, made in particular by turns, in a user and/or peripheral ID code can be taken into account for the sake of the authorization and/or authentication. Preferably by means of the authorization checking devices, a check of the authentication and/or authorization of the user, the access peripherals and/or storage devices for an intended access can be performed.

The capability of using the data in the personal data archive system of the invention is still further optimized by providing that the storage devices contain a plurality of regions with which different access security means, such as password, PINs, or the like can be associated.

A special further protection can advantageously be provided in the invention for writing accesses, in that storing new or modified data in the storage devices can be done there only together with a signature after the inputting of this signature, and that the signature can be generated, in particular automatically, preferably by means of a user and/or access peripheral ID code.

Below, a few further preferred embodiments will be described that result from various combinations of the dependent claims.

As the patient card, a processor chip card can for instance be used, which contains both at least some of the authorization checking devices in the form of a processor and a first group of storage devices on the chip, in order to form a patient data archive system. With this kind of processor chip card, the exchange of information in the medical field can be improved. Primarily, the processor chip card serves as a control and security element, and the memory function is secondary, especially because of the typically low storage capacity of such cards. The system according to the invention therefore includes along with the card a mobile data store per se, for which a magnetooptical disk in the form of a 2.5 inch diskette is suitable, as an example. These data carriers are as small and as easy to handle as a chip card but have a storage capacity of 140 MB, for instance, and are rewritable.

The security created by the invention is attained technologically by the combination of the processor chip card with a mass data store that is external to the processor chip card. Access to the mass data store is attained solely via the processor chip card with its security devices for authorization checking and access enablement. Thus the data on the magnetooptical disk, for instance, are protected just as well as if they were stored on the processor chip card itself.

Thus a patient, in this age of increasing medical fragmentation, has more than merely a medical ID card and is made capable of documenting his own relevant illness data completely, so that he can then make these data available to a particular attending physician or his insurance organization. The comprehensive personal and in particular medical data collection in the hands of the patient, which thus becomes generally possible by means of the invention, contributes, to an improvement in the exchange of information, for instance between physicians. At the same time, to remain with the example of the patent data archive system, it is an instrument for quality assurance of medical services and contributes to full-range care of the patient. The avoidance of data losses when a patient changes positions, for instance, leads to fewer tests being required and hence is better for the patient's health and less expensive to insurers.

However, a data collection regarding the disease history must not be exhausted with a listing of patient history, diagnoses or examinations performed. Every later attending physician would like to see at least the full reports from the physician and hospital, and often he will understandably not want to omit being able to see the original records and findings as well. Such a comprehensive data collection would not be feasible on a conventional processor chip card alone, however, but is feasible only in combination with a typical data store, for which, without the invention, there would be no adequate data protection.

In a continuation of the above-described exemplary embodiment, the processor chip card can function first as an emergency ID card. Along with the typical emergency data, the appropriate memory group can also be used to store an organ donor card or emergency living will, if desired. Possible rules of access to this have already been described above. By the collaboration of the owner via an access key, such as a password or a PIN, a comprehensive ID card containing the essential medical basic data (or in other applications, financial, insurance, "petty cash" data) is the result. Together with the mass storage medium, which may for instance be electronic, for the complete data the patient receives a complete collection of important illness data; the physician's records, images (such as X-rays and sonograms) and biosignals (EKGs, etc.) are present in the original. For practical reasons, when access is enabled for a physician who has identified himself for instance with a physician's card, along with his card reader and his disk drive, to the authorization checking devices, the collaboration of the patient can be restricted to a photograph of the patient showing him as the card owner on the processor chip card.

An arrangement that operates automatically may also be provided that assures that the memory of a filled processor chip card is ready to receive additional new data again by moving data for storage to an associated MO disk, for instance.

In embodying the processor chip card as a control and security instrument, it is possible to equip it with a coprocessor, by means of which for the security concept an authentication of the terminal, card and user and also documentation about every access to the stored data can be made.

As the authorization checking devices and their checking means, processor devices in particular can be named, in some or generally in all the storage devices and/or in a control computer or access peripheral, along with suitable programs and ID codes for access peripherals, storage devices, the owner, and users. Security can also be attained, or in addition, by providing that the ID codes of separate storage devices and in particular data carriers must be combined in order to be able to gain access to protected data. Moreover, the data can be contained directly in executable program data files, the callup of which depends on certain ID codes. The fundamental protection according to the invention is attained, however, because access depends on the outcome of checking on the part of the authorization checking devices.

Admittedly, the system of the invention cannot replace a physician's data file, if for no other reason because of the existing duty of documentation. However, the invention provides an important capability of supplementation, for instance of the physician's card file, since by means of the patient data archive system, all the relevant data are available, complete, unadulterated, and directly. Another argument for digital archiving is that numerous data even now, but surely in the future, will be present from the very outset in digital form, examples being X-rays, sonograms, EKGs, EEGs, physician's records, and so forth.

Other advantageous and preferred features of the invention will become apparent from the claims and combinations among them.

BRIEF DESCRIPTION OF THE DRAWINGS

Details of the invention will be described further below in conjunction with the drawings, in which:

FIGS. 2a–2c are charts showing possible ways of dividing up the storage devices.

DETAILED DESCRIPTION OF THE INVENTION

Figure 1:
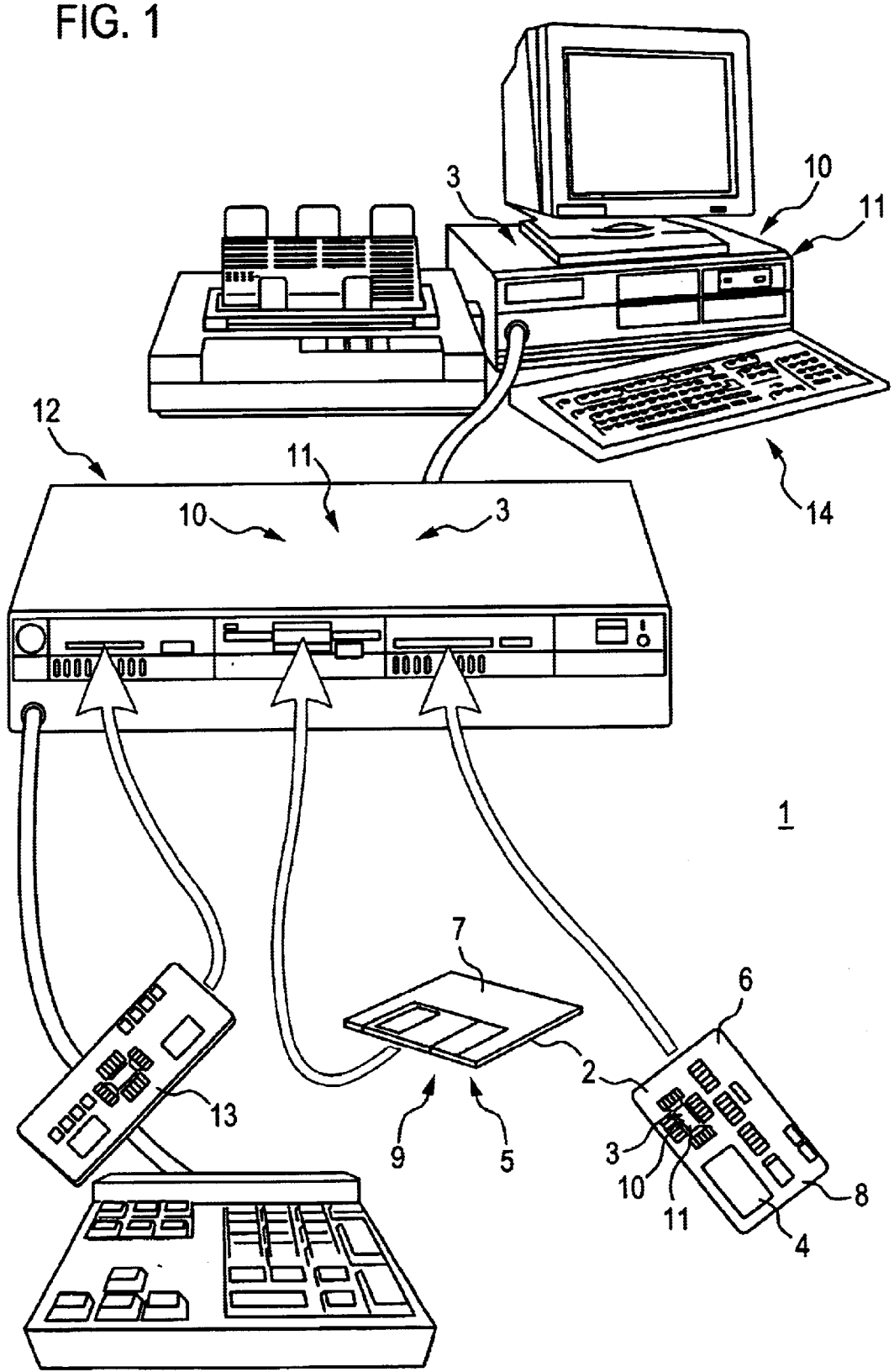
FIG. 1 shows a schematic illustration of system components of a personal data archive system.
Figure 3:
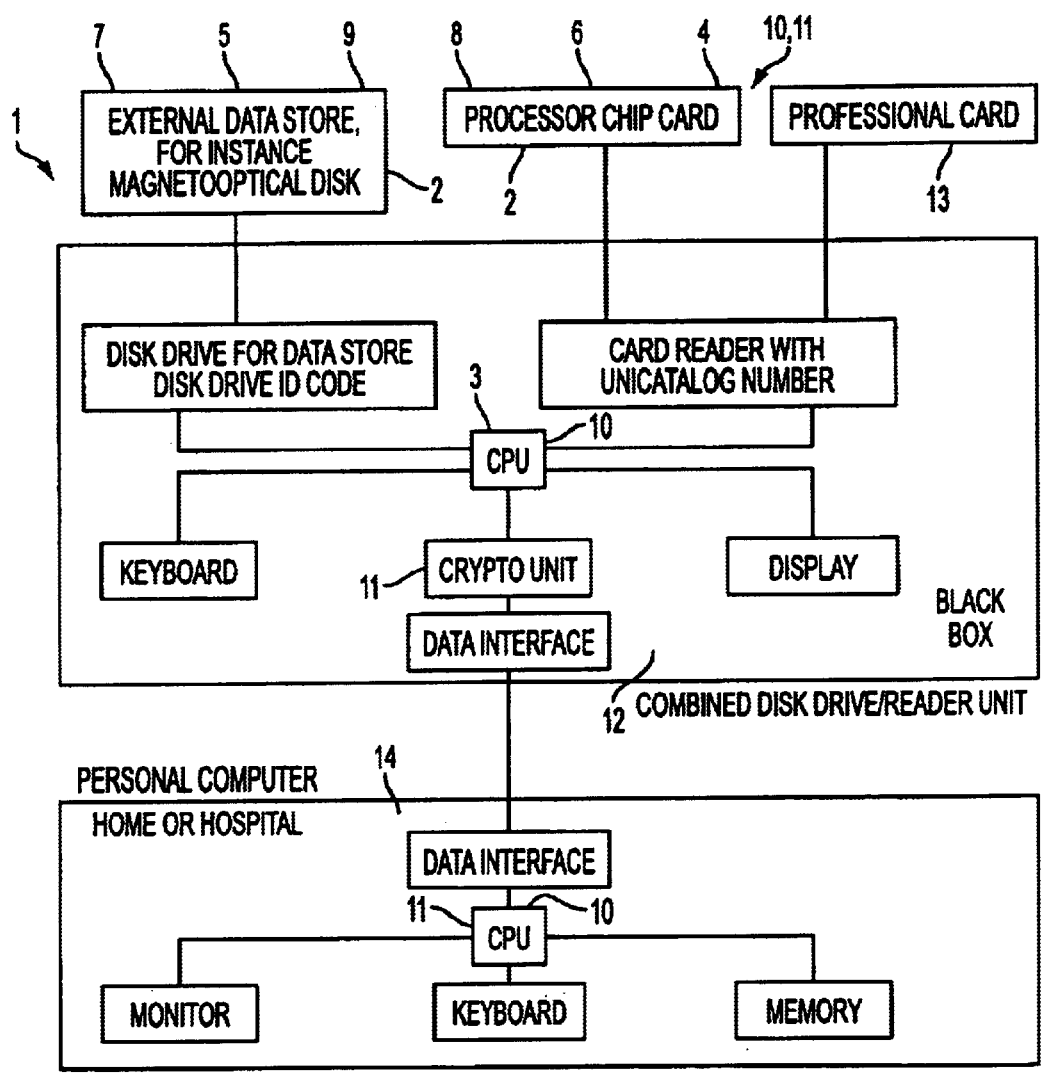
FIG. 3 is a block circuit diagram of the layout of FIG.1.

In FIGS. 1 and 3, a personal data archive system 1 is shown. The system 1 contains portable or mobile personal storage devices 2 for entering and storing personal data with the owner. The storage devices contain first and second separate data carriers 8 and 9, which form individual memory devices in the form of first and second groups 6 and 7, respectively, of storage devices 2.

For access to the individual data carriers 8, 9, an access peripheral 12 is suitable; it represents a combined reader and disk drive for the two data carriers 8, 9. The access peripheral 12 is also designed for reading an authorization card 13.

The first data carrier 8 is a processor chip card and serves both to store smaller amounts of data, such as an emergency ID card, overview data and/or treatment data of the owner in memory as well as tracking data of memory accesses accomplished, and as a component of authorization checking devices 3, for which the processor devices 10 of the card are used. As FIG. 3 clearly shows in particular, additional processor devices 10 are provided in the access peripheral 12, which are likewise a component of the authorization checking devices 3 for ascertaining access authorization.

The second data carrier 9 is a magnetooptical disk and thus makes it possible to store large amounts of data in memory for storing detail data. A control is also provided by means of the processor devices 10, in order to prevent the memory of the processor chip card from being full and unable to receive any further data; to that end, data are repeatedly transferred from the processor chip card to the magnetooptical disk.

The authorization checking devices 3 associated with the storage devices 2 serve the purpose of data security, since they assure that access to at least some of the personal data stored in the personal storage devices 2 can be enabled only as a function of a positive authorization and/or authentication. In the exemplary embodiment shown, the individual processor devices 10 are responsible for this, along with ID codes described in further detail hereinafter.

The authorization checking devices 3 of the exemplary embodiment shown are embodied such that they take into account a change of ID codes for users and/or peripherals in turns for the sake of authorization and/or authentication and perform a check of authenticity and/or authorization of the user, access peripherals and storage devices 2 for an intended access. Writing accesses to the storage devices 2 can also be stored in memory there only along with a signature after the signature is entered; this signature is generated automatically by a user or access peripheral ID code, by using the RSA process.

The archive system 1 shown is designed such that access to the second group 7 of storage devices 2 can be gained only in combination with the first group 6 of storage devices 2. Various checking and authorization steps are also provided in order to govern access to various data regions.

In a first checking step, only a reader ID code is checked, in order to allow access to emergency data. In this step or a higher checking step, an authorization card may optionally be required for access to data that in turn provide an overview of further personal data of the chip card owner. A further checking step can be realized by providing that personal data, such as detail data, stored in the second group 7 of personal storage devices 2 can be accessed only as a function of a positive authorization and/or authentication by the authorization checking devices 3. Such an identification or ID code may take into account the following information, either alone or combined: a reader ID code, a disk drive ID code, a data carrier ID code, a user ID code, and an owner ID code. These last two, in particular, can also be in the form of PINs (personal identification numbers) or secret numbers, or the like, and different inputs can lead to different authorization steps. The various checking steps of the authorization checking devices 3 may for instance also be used to grant different authorizations for writing access and reading access.

In conjunction with the card reader, the authenticity of the processor chip card is checked by the authorization checking devices 3. Counterfeit cards, for instance, can then be rejected. Using the processor chip card, a check of the card reader is also done by the authorization checking devices 3, 1so that unauthorized readers gain no access whatever to the data of the processor chip card or of the mass store. A similar mutual authorization check may also be contemplated for the magnetooptical disk and the corresponding disk drive.

In detail, the identification characteristics of the card reader (such as the unicatalog number) and of the disk drive for the magnetooptical disk are detected (disk drive ID code, for instance) and the corresponding data are stored on or in the memory of the processor chip card as soon as the reader or the disk drive accesses stored data. Should the capacity of the corresponding memory on the processor chip card not suffice, then older data are transferred to the MO disk or erased. By acquisition of user identification (user and owner ID codes), each access to the stored data is detected separately for the processor chip card and the MO disk. Alternatively or as a supplement to other identification characteristics, such as the reader ID code or a user ID code, an authorization card can furnish required data for authorization checking, data that the user can show and that can also be stored so that wherever various users access the same card reader, as in an emergency vehicle, it is possible to perform simple, fast and secure authorization identification.

The comprehensive data on the second group 7 of storage devices 2,1 such as image data on the MO disk, can be read only whenever a user has appropriate program parts, for instance, which however is not possible until after a positive authentication check.

As a further security aspect, in the example shown the access peripheral 12 includes crypto devices 11, which provide for decryption and encryption in reading or writing accesses to groups 6 and 7 of the storage devices 2 and which to process large amounts of data contain at least one crypto processor, for instance, designed as a coprocessor. The crypto devices 11 precede the storage devices 2 and are enabled in operation by means of the authorization checking devices 3 to process accesses to the storage devices 2. The data transferred among individual memory devices or their access peripherals 12 and computer devices 14 are decrypted or encrypted by the crypto unit, which likewise does not come into operation until after an authentication check has an a positive outcome. When a data file on the MO disk is called up, it is automatically decrypted. Conversely, an automatic encryption of a data file takes place when it is written on the MO disk. The corresponding data file names are not readable in the system 1 without enablement by the authorization checking devices 3 and are stored on the processor chip card. The high data transfer rate can be handled by the independent crypto unit.

The first group of storage devices 2 or the first memory device 6 is not limited to the embodiment described above; instead, the data carrier 8 may be a magnetic, magnetooptical or optical storage area or a memory chip, especially on or in a plastic card that is preferably approximately the size of a credit card. The embodiment of the second group of storage devices 2 or the second memory device 7 is likewise not limited to a magnetooptical disk but instead may be any electronic, magnetic, magnetooptical or optical mass store, especially in the form of a 2.5 inch or 3.5 inch diskette or a PCMCIA unit as the data carrier 9.

The storage devices 2 are each formed by a storage medium 4, 5, corresponding to the data carriers 8, 9, that can be rewritten by adding and/or modifying personal data. For certain applications at least portions of the two writable storage media 4, 5 are write-protected or write-protectable. As a result, invariable entries can for instance be protected again being overwritten by mistake. Regions of the storage medium 5 of the second data carrier can be write-protected or write-protectable for the same reason, for instance to preclude later alterations of the access documentation.

The processor devices 10, in addition to their task of authorization checking, also perform the control of at least some of the storage devices 2 and/or at least some of the control of accesses to them.

Copy protection devices, printout protection devices and output limitation devices, which prevent undesired copying, printing or other kinds of output of data taken from the storage devices 2, if these corresponding devices are not neutralized or in other words turned off with regard to the authorization checking devices by means of a suitable authorization tracking, are not shown specifically here.

Instead of or in addition to the access peripheral 12 shown, separate access peripherals may be provided both for the individual data carriers 8 and 9 and for the authorization card 13, examples being personal, mobile and/or stationary access peripherals. The access peripheral 12, both for the processor chip card and the magnetooptical disk, is designed in minidisk form for writing and/or reading access.

Any usable access peripheral 12 expediently contains card readers, to suit the formats of data carriers that receive the storage devices 2, examples being magnetic strip or chip cards, disk drives for magnetic, magnetooptical or optical disks, CD ROM drives, and/or receptacles for PCMCIA units. Even if the access peripherals 12 for the first and second groups 6, 7 of the storage devices 2 are embodied separately, these peripherals 12 can be combined and via this combination, a suitable authorization tracking can be detected by the authorization checking devices 3.

To produce backup copies that prevent complete data loss if the storage devices 2 crash, the access peripherals 12 directly, or the authorization checking devices 3 without authorization tracking, allow the production of backup copies of the portable personal storage devices 2. To that end, volatile memory devices may for instance be contained in the corresponding access peripheral 12, to buffer-store data for copying.

As can also be seen from FIGS. 1 and 3, a computer device 14 in the form of a PC is provided for driving the access peripheral 12. These computer devices 14 also serve as display and input/output equipment for data, both for the authorization checking devices 3 and the storage devices 2, in order to search for data and output and enter it.

The access peripheral 12 shown in FIG. 1 is connected via one line to its own keyboard, not identified by reference numeral, and via another line to suitable data interfaces with the computer devices 14. The computer keyboard and/or the access peripheral keyboard can be used to input pins and the like. The access peripheral 12 is also provided with display devices, not identified by reference numeral.

The first data carrier 8 is at the same time a health insurance card, and the entire system 1 serves to archive patient data, including both written and graphic documentation, in the hands of the owner. Other data may, also be archived with this or similar systems, examples being financial data, insurance data, travel data, and many others.

Figure 2A:
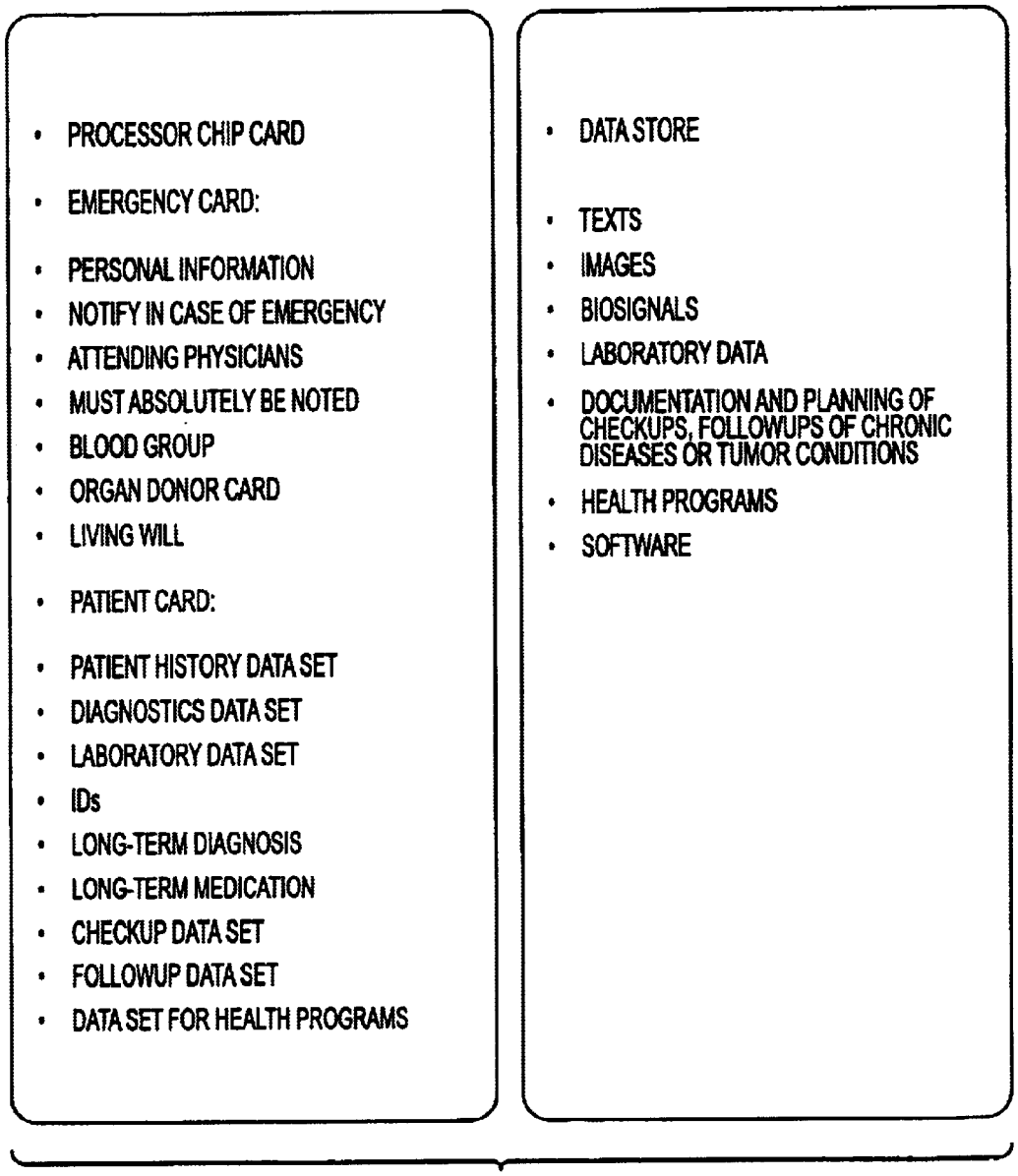

For the specific application of the patient data archive system, FIGS. 2a–2c tabulate a memory organization. FIG. 2a shows the organizational structure of the two data carriers, FIG. 2b shows information on the content of the emergency card included, and FIG. 2c explains the content of the patient card; the various memory regions are designated directly, so that no further explanation is needed to understand them. In actual use, individual fields and entries can be called up via the computer devices 14 using menus or windows.

Although above reference has been made to a patient data archive system, patient data and the medical field in general, this is understood to be merely an example. The invention relates to a personal data archive system that is defined by the characteristics and combinations of characteristics recited in the claims and is not limited to individual exemplary embodiments of the description. For instance, more than two (separate) groups of storage devices may be provided, for instance, in a single processor card may for instance cooperate with a plurality of MO disks each for its own subject-matter area. In particular, all the embodiment possibilities of the invention contained in the wording of characteristics in the claims, without limitations and with the modifications and substitutions within the competence of one skilled in the art, are covered by the scope of the invention.

LIST OF REFERENCE NUMERALS

1 Personal data archive system
2 Storage devices
3 Authorization checking devices
4, 5 Storage medium
6 First group of storage devices
7 Second group of storage devices
8, 9 First and second data carriers
10 Processor devices
11 Crypto devices
12 Access peripherals
13 Authorization card, or physician's or rescue service card
14 Computer devices

What is claimed is:

1. A personal data archive system comprising:
 a first portable memory device containing personal data solely of a single owner;
 a second portable memory device of greater data storage capacity than and differing from said first portable memory device, said second portable memory device containing additional personal data associated solely with said single owner, wherein said second portable memory device is separate from said first portable memory device, and a full set of personal data consists of data of the single owner stored on said first and second portable memory devices; and
 at least one authorization-checking device associated with said first and second portable memory devices in order to access data stored on each memory device wherein the authorization-checking device can be enabled only as a function of a positive authorization and authentication process; and
 wherein the first portable memory device is accessible independent of the second memory device, and the full set of unique, personal data belonging to a single owner is accessible only when the first portable memory device is used in combination with the second portable memory device and only after a positive authorization and authentication process is performed through said authorization checking device.

2. The personal data archive system of claim 1, further comprising a plurality of checking steps performed by a plurality authorization-checking devices as a function of a positive authorization and authentication process.

3. A The personal data archive system of claim 1, wherein at least one of said portable memory devices is formed by a storage medium that can be written and rewritten for modifying the owner's data.

4. The personal data archive system of claim 3, wherein said authorization checking device is designed to enable at least one reading access and writing access to said writable storage medium as a function of the positive authorization and authentication process.

5. The personal data archive system of claim 3, wherein at least some of the writable storage medium of the at least one portable memory device is write-protected or write-protectable.

6. The personal data archive system of claim 1, wherein the first portable memory device and the second portable memory device have different storage capacities.

7. The personal data archive system of claim 6, wherein the first portable memory device has the smallest capacity and is Ian ID, identification or master portable data memory device.

8. The personal data archive system of claim 6, wherein the data stored in the first portable memory device is accessible for identification purposes only after a positive authorization and authentication process, as part of a first checking step of the authorization checking device.

9. The personal data archive system of claim 6, wherein the second portable memory device has a greater capacity than the first portable memory device and stores detail data associated with the single user.

10. The personal data archive system of claim 1, wherein the first portable memory device is a magnetic, magnetooptical, optical memory area or memory chip in an approximately credit-card-sized plastic card data carrier.

11. The personal data archive system of claim 10, further comprising a processor device wherein the processor device controls or partially controls access to at least one of the following: at least one of the portable memory devices, at least one authorization checking device.

12. The personal data archive system of on of claim 1, wherein the second portable memory device is a magnetic, magnetooptical, electronic, or optical mass storage unit in the form of a 2.5 or 3.5 inch diskette or a PCMIA unit as a data carrier.

13. The personal data archive system of claim 1, further comprising a processor device associated with at least one of said first and second portable memory devices and forming at least one authorization checking device, said processor device being disposed on the data carrier of at least one of said portable memory devices.

14. The personal data archive system of 1, further comprising:
 crypto devices wherein the crypto devices precede the portable memory devices and are enabled by the authorization-checking devices for processing access to the portable memory devices.

15. The personal data archive system of claim 14, further comprising a processor device wherein the crypto devices are part of said processor device.

16. The personal data archive system of claim 1, further comprising:
 access peripherals with peripheral identification codes, wherein the authorization checking devices incorporate the peripheral identification codes of the access peripherals for manipulating the portable memory devices as part of a checking step in the positive authorization and authentication process.

17. The personal data archive system of claim 1, further comprising:
 portable memory device identification (ID) codes, wherein the portable memory devices ID codes are incorporated by the authorization checking device into a checking operation as part of the positive authorization and authentication process.

18. The personal data archive system of claim 1, further comprising:
 a user identification (ID) code wherein the user's (ID) code is incorporated by the authorization checking device in a checking step as a part of the positive authorization and authentication process to enable access to at least some of the personal data stored in the portable memory devices.

19. The personal data archive system of claim 18, further comprising manual and electronic inputs to perform owner identification for the authorization checking device.

20. The personal data archive system of claim 19, further comprising an authorization card for use with said inputs to perform user identification for the authorization checking device.

21. The personal data archive system of claim 18, further comprising:
 access peripherals with access peripheral identification (ID) codes, wherein access is enabled by one of said access peripheral ID codes and the identification codes of a user of said access peripheral in conjunction with the authorization checking device.

22. The personal data archive system of claim 21, further comprising:
 access peripherals with access peripheral identification (ID) codes wherein the peripheral ID code is activatable by means of a user ID code that can be input into at least one access peripheral in a positive authorization and authentication process, the peripheral ID codes can be detected by the authorization checking devices for checking authorization and authentication.

23. The personal data archive system of claim 22, wherein changes in a user ID and peripheral ID code can be made and the authorization checking device takes the changes into account when processing the authorization and authentication process.

24. The personal data archive system of claim 21, further comprising:
a digital signature which is input and then stored with a user ID and a peripheral ID code on a portable memory device.

25. The personal data archive system of claim 1, further comprising personal access peripherals wherein the owner of personal data archived in the portable memory accesses at least some of the personal data for one of data modification/supplementation and transmittal via remote data transmission upon a positive authorization and authentication process.

26. The personal data archive system of claim 25, wherein the access peripherals are designed for read/write access to at least some of the personal data stored in the personal portable memory devices when a positive authorization and authentication is performed.

27. The personal data archive system of claim 25, further comprising card readers, disk drives, CD-ROM drives or receptacles for PCMIA units contained within the access peripherals.

28. The personal data archive system of claim 25, wherein the access peripherals are designed to produce backup copies of the portable memory devices in a first checking step of the authorization and authentication process.

29. The personal data archive system of claim 1, further comprising:
mobile access peripherals and stationary access peripherals for associating the data from the first and second portable memory devices, where a user who performs a positive authorization and authentication process can access the full set of data and implement data modification/supplementation.

30. The personal data archive system of claim 1, further comprising at least two access peripherals which are combined to interconnect corresponding data carriers of the portable memory devices wherein this combination is detectable by the authorization and authentication process.

31. The personal data archive system of claim 1, wherein the unique data associated with the single owner is patient data, including written and graphic documents.

32. The personal data archive system of claim 31, further comprising a third portable memory device for emergency personnel wherein the first portable memory device includes an emergency data storage region which stores emergency data of the owner, which may include administration data and the data of an emergency card, organ donor card, or emergency living will, and access to the emergency data can be enabled by one of said third portable memory device, a physician/rescue service peripheral ID and an owner ID code, thereby permitting access only to the first portable memory device.

33. The personal data archive system of claim 32, wherein the first portable memory devices comprises an overview data store region, including a listing of important patient history, any administration of blood or blood products that may have been made and a documentation of important health and disease data, including allergy, immunization, x-ray, pacemaker, diabetic, and medication data; the stored overview data being similar to a patient's medical file, and access to the stored overview data can be enabled by the authorization checking devices in combination with one of said third portable memory devices, a special physician/rescue service access peripheral ID code and an owner ID code for access only to the said first portable memory device.

34. The personal data archive system of claim 32, wherein the first portable memory device further includes a treatment data storage region, including storage for a predetermined time frame and a predetermined content structure of check-ups and medical examinations and access to said treatment data storage region can be enabled by the authorization checking devices by one of said third portable memory device, a special physician access peripheral ID code and an owners' ID code for access only to said first portable memory device.

35. The personal data archive system of claim 32, wherein the first portable memory device further includes a tracking data storage region, in which at least one of a predeterminable number and type of accesses to the portable memory devices can be stored individually and to which access can be enabled by the authorization checking device in combination with one of said third portable memory device, a special physician access peripheral ID code and an owners ID code for access only to said first portable memory device.

36. The personal data archive system of claim 35, wherein the tracking data storage region is a shift register embodied in the first portable memory devices so that the oldest content therein can be shifted to create space for a new entry in the tracking data storage region in the first portable memory devices.

37. The personal data archive system of claim 32, wherein the second portable memory device contains a tracking data storage region, in which at least one of a predeterminable number and type of accesses to the full set of data contained on the portable memory devices, and the individual authorization and authentication performed and the type of accesses enabled by the authorization checking devices are stored, and access to the tracking data storage region can be enabled by the authorization checking devices in combination with one said a third portable memory device, a special physician access peripheral ID code and an owner's ID code for access only to said first portable memory device.

38. The personal data archive system of claim 1, wherein the portable memory devices are a component of a health insurance card, personal ID card, or ATM card.

39. The personal data archive system of claim 1, wherein the authorization checking device performs a check of the authentication and authorization of the user, the access peripherals and portable memory devices before enabling an intended access.

40. The personal data archive system of claim 1, wherein the portable memory devices contain a plurality of access security means.

41. A personal data archive system comprising:
a first portable memory device containing personal data solely of a single owner;
a second portable memory device having greater data storage capacity than and differing from said first portable memory device, said second portable memory device containing additional personal data associated solely with said single owner, wherein said first, second and third portable memory devices are separate from each other, and a full set of personal data consists of the data of said single owner stored on said first, second and third portable memory devices; and a third portable memory device containing data solely of a health care professional;

at least one authorization-checking device associated with said first, second, and third portable memory devices in order to access data stored on each memory device, wherein the authorization-checking device can be enabled only as a function of a positive authorization and authentication process; and wherein the first and third portable memory devices are accessible independent of the second memory device, and the full set of unique, personal data belonging to a single owner is accessible only when the first and second portable memory devices are used in combination with the third portable memory device and only after a positive authorization and authentication process is performed through said at least one authorization checking device.

* * * * *